US010638940B2

(12) United States Patent
Witschey et al.

(10) Patent No.: US 10,638,940 B2
(45) Date of Patent: May 5, 2020

(54) ASSESSMENT OF HEMODYNAMIC FUNCTION IN ARRHYTHMIA PATIENTS

(71) Applicant: The Trustees of the University of Pennsylvania, Philadelphia, PA (US)

(72) Inventors: Walter R. T. Witschey, Philadelphia, PA (US); Francisco Contijoch, San Diego, CA (US); Robert C. Gorman, Lower Gwynedd, PA (US); Yuchi Han, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 840 days.

(21) Appl. No.: 15/015,373

(22) Filed: Feb. 4, 2016

(65) Prior Publication Data

US 2016/0228014 A1 Aug. 11, 2016

Related U.S. Application Data

(60) Provisional application No. 62/113,116, filed on Feb. 6, 2015.

(51) Int. Cl.
*A61B 5/00* (2006.01)
*A61B 5/02* (2006.01)
*A61B 5/055* (2006.01)
*A61B 5/0452* (2006.01)
*A61B 5/0402* (2006.01)

(52) U.S. Cl.
CPC ........ *A61B 5/02028* (2013.01); *A61B 5/0044* (2013.01); *A61B 5/0452* (2013.01); *A61B 5/055* (2013.01); *A61B 5/7289* (2013.01); *A61B 5/0402* (2013.01); *A61B 2576/023* (2013.01)

(58) Field of Classification Search
CPC ... A61B 5/02028; A61B 5/0452; A61B 5/055; A61B 5/0044; A61B 5/7289; A61B 5/0402; A61B 2576/023
See application file for complete search history.

(56) References Cited

U.S. PATENT DOCUMENTS

| 9,081,882 B2 * | 7/2015 | Taylor | A61B 5/02007 |
| 2015/0051479 A1 * | 2/2015 | Pipe | A61B 5/055 600/416 |
| 2015/0126850 A1 * | 5/2015 | Cetingul | G01R 33/56 600/413 |

(Continued)

OTHER PUBLICATIONS

Bacharach et al., "Comparison of Fixed and Variable Temporal Resolution Methods for Creating Gated Cardiac Blood-Pool Image Sequences", The Journal of Nuclear Medicine, Jan. 1990, vol. 31, No. 1, 38-42.

(Continued)

*Primary Examiner* — Joel Lamprecht
(74) *Attorney, Agent, or Firm* — BakerHostetler

(57) ABSTRACT

Electrocardiogram (ECG)-gated cardiac magnetic resonance imaging (MRI) alone may be unable to capture the hemodynamics associated with arrhythmic events. As a result, values such as ejection fraction are acquisition dependent. The desired RR-duration determines the arrhythmia rejection. By combining real-time volume measurements with ECG recordings, beat morphologies can be categorized and a more comprehensive evaluation of ventricular function during arrhythmia can be provided.

20 Claims, 10 Drawing Sheets

(56) References Cited

U.S. PATENT DOCUMENTS

2015/0192653 A1* 7/2015 Sharif .................... A61B 5/055
  600/420
2015/0276909 A1* 10/2015 Kawaji .............. G01R 33/5673
  600/413

OTHER PUBLICATIONS

Bauer et al., "True real-time cardiac MRI in free breathing without ECG synchronization using a novel sequence with radial k-space sampling and balanced SSFP contrast mode", Int J Cardoivasc Imaging, 2013, 29, 1059-1067.

Cha et al., "Premature Ventricular Contraction-Induced Cardiomyopathy", Circ Arrhythm Electrophysiol, Feb. 2012, 229-236.

Chia et al., "Performance of QRS Detection for Cardiac Magnetic Resonance Imaging with a Novel Vectorcardiographic Triggering Method", Journal of Magnetic Resonance Imaging, 2000, 12, 678-688.

Contijoch et al., "User-initialized active contour segmentation and golden-angle real-time cardiovascular magnetic resonance enable accurate assessment of LV function in patients with sinus rhythm and arrhythmias", Journal of Cardiovascular Magnetic Resonance, 2015, 17, 37, 1-12.

Del Carpio Munoz et al., "Characteristics of premature Ventricular Complexes as Correlates of Reduced Left Ventricular Systolic Function: Study of the Burden, Duration, Coupling Interval, Morphology, and Site of Origin of PVCs", Journal of Cardiovascular Electrophysiology, Jul. 2011, vol. 22, No. 7, 791-798.

Feng et al., "Golden-Angle Radial Sparse Parallel MRI: Combination of Compressed Sensing, Parallel Imaging, and Golden-Angle Radial Sampling for Fast and Flexible Dynamic Volumetric MRI", Magnetic Resonance in Medicine, 2014, 72, 707-717.

Hamlet et al., "Effect of variable breath-hold positions during cardiac magnetic resonance on measures of left ventricular mechanics", Journal of Cardiovascular Magnetic Resonance, Jan. 2014, 16(Suppl. 1), P78.

Hansen et al., "Retrospective Reconstruction of High Temporal Resolution Cine Images from Real-Time MRI Using Iterative Motion Correction", Magnetic Resonance in Medicine, 2012, 68, 741-750.

Hansen et al., "Gadgetron: An Open Source Framework for Medical Image Reconstruction", Magnetic Resonance in Medicine, 2013, 69, 1768-1776.

Huizar et al., "Left Ventricular Systolic Dysfunction Induced by Ventricular Ectopy", Circ Arrhythm Electrophysiol, Aug. 2011, 543-549.

Kühl et al., "Assessment of Myocardial Function with Interactive Non-Breath-hold Real-time MR Imaging: Comparison with Echocardiography and Breath-hold Cine MR Imaging", Radiology, 2004, vol. 231, No. 1, 198-207.

Lustig et al., "Sparse MRI: The Application of Compressed Sensing for Rapid MR Imaging", Magnetic Resonance in Medicine, 2007, 58, 1182-1195.

Olgun et al., "The role of interpolation in PVC-induced cardiomyopathy", Heart Rhythm, Jul. 2011, vol. 8, No. 7, 1046-1049.

Pan et al., "A Real-Time QRS Detection Algorithm", IEEE Transactions on Biomedical Engineering, Mar. 1985, vol. BME-32, No. 3, 230-236.

Potfay et al., "Abnormal Left Ventricular Mechanics of Ventricular Ectopic Beats", Circ Arrhythm Electrophysiol, Oct. 2015, 16 pages.

Pruessman et al., "Advances in Sensitivity Encoding With Arbitrary k-Space Trajectories", Magnetic Resonance in Medicine, 2001, 46, 638-651.

Sørensen et al., "Real-Time Reconstruction of Sensitivity Encoded Radial Magnetic Resonance Imaging Using a Graphics Processing Unit", IEEE Transactions on Medical Imaging, Dec. 2009, vol. 28, No. 12, 1974-1985.

Sun et al., "The influence of premature contractions on left ventricular function in asymptomatic children without structural heart disease: an echocardiographic evaluation", The International Journal of Cardiovascular Imaging, 2003, 19, 295-299.

Suzuki et al., "Ventricular contractility in atrial fibrillation is predictable by mechanical restitution and potentiation", The American Physiological Society, 1998, H1513-H1519.

Tabata et al., "Assessment of LV systolic function in atrial fibrillation using an index of preceeding cardiac cycles", Am J Physiol Heart Circ Physiol, 2001, 281, H573-H580.

Takada et al., "Experimental Studies on Myocardial Contractility and Hemodynamics in Extrasystoles", Japanese Circulation Journal, May 1970, vol. 34, 419-430.

Wang et al., "Cellular mechanism of premature ventricular contraction-induced cardiomyopathy", Heart Rhythm, Nov. 2014, vol. 11, No. 11, 101-110.

Witschey et al., "A Real-Time Magnetic Resonance Imaging Technique for Determining Left Ventricle Pressure-Volume Loops", Ann Thorac Surg., May 2014, 97(5), 1597-1603.

Yamaguchi et al., "Pressure-Interval Relationship Characterizes Left Ventricular Irregular Beat Contractilities and Their Mean Level during Atrial Fibrillation", Japanese Journal of Physiology, 1997, 47, 101-110.

Yarlagadda et al., "Reversal of Cardiomyopathy in Patients With Repetitive Monomorphic Ventricular Ectopy Originating From the Right Ventricular Outflow Tract", Circulation, Aug. 2005, 112(8), 1092-1097.

* cited by examiner

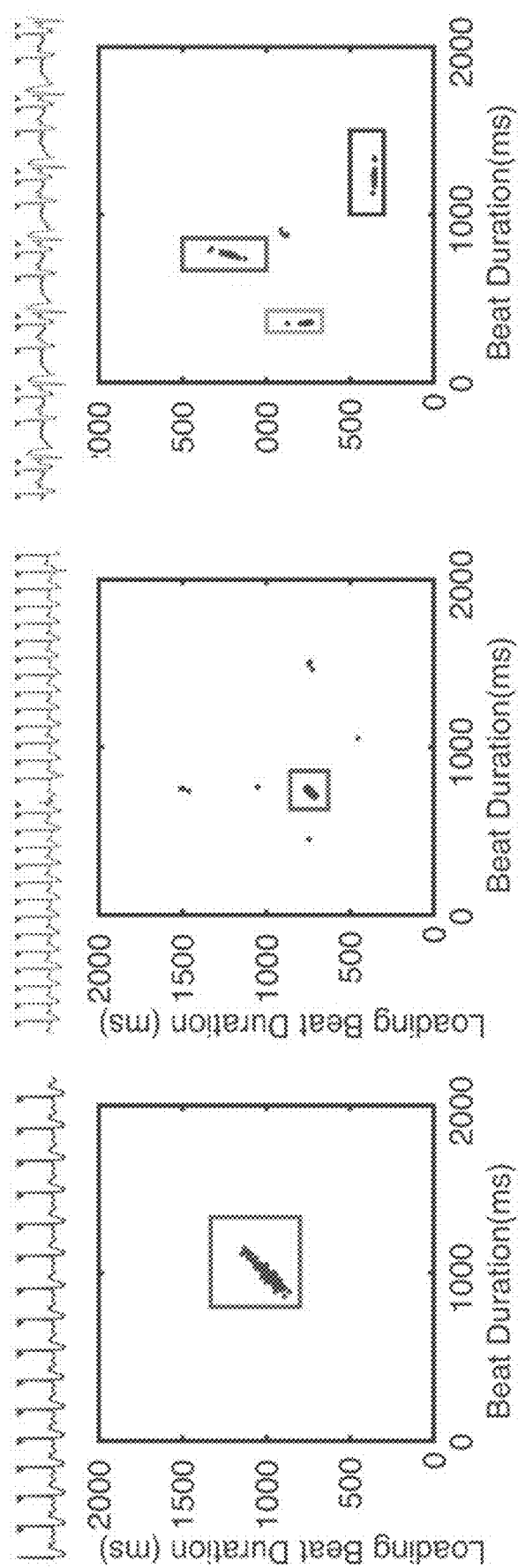

ASSESSMENT OF HEMODYNAMIC FUNCTION IN ARRHYTHMIA PATIENTS

RELATED APPLICATION

This application claims the benefit of, and hereby incorporates by reference, U.S. Provisional Application No. 62/113,116 entitled "ASSESSMENT OF HEMODYNAMIC FUNCTION IN ARRHYTHMIA PATIENTS", filed Feb. 6, 2015.

GOVERNMENT RIGHTS

This invention was made with government support under grant numbers HL108157 and HL120580 awarded by the National Institutes of Health. The government has certain rights in the invention.

TECHNICAL FIELD

The invention relates to the development of imaging methods for patients with cardiovascular arrhythmias and, in particular, an image based method to assess hemodynamic function in arrhythmia patients.

BACKGROUND

Electrocardiogram (ECG)-gated cardiac magnetic resonance imaging (MRI) is the gold standard for volumetric evaluation of patients. Cardiovascular Magnetic Resonance imaging (CMR), sometimes known as cardiac MRI, is a medical imaging technology for the non-invasive assessment of the function and structure of the cardiovascular system. It is derived from, and based on, the same basic principles as magnetic resonance imaging (MRI) but with optimization for use in the cardiovascular system. These optimizations are principally in the use of ECG gating and rapid imaging techniques or sequences. By combining a variety of such techniques into protocols, key functional and morphological features of the cardiovascular system can be assessed.

Imaging of the heart allows for mathematical expressions defining flow of blood in and out of the heart. Cardiac imaging uses visually enhanced mathematics of the folding and unfolding of the myocardium focused on a single cardiac cycle.

Clinically, ejection fraction (EF) is used as a surrogate for function. Ejection fraction is the fraction of outbound blood pumped from the heart with each heartbeat. It is a general measure of a person's cardiac function. Ejection fraction is typically low in patients with systolic congestive heart failure.

SUMMARY

Cardiac functional parameters, such as ejection fraction, which might be determined from non-invasive imaging, are biomarkers used for a range of clinical decisions from pacemaker implantation to surgical survival. Patients with irregular rhythms are assigned a single value for these parameters. However, this single valued parameter does not take into account the relative frequency or category of heartbeat morphologies if the patient has an arrhythmia. Consequently, important clinical decisions in these patients, such as whether to have an implantable cardioverter defibrillator (ICD) implanted, are based on potentially incorrect or incomplete knowledge of the true parameters.

Cardiac arrhythmia (also known as irregular heartbeat) is any of a group of conditions in which the electrical activity of the heart is irregular, faster, or slower than normal. An ECG-gated cardiac MRI can use arrhythmia rejection. If an irregular heartbeat causes some R-R intervals to be too short, data from these shorter heart beats can be rejected in an arrhythmia rejection process so that the resulting images represent a regular heartbeat.

The inventors have determined that the use of arrhythmia rejection in the presence of ectopic beats (such as a premature ventricular contraction, or a premature atrial contraction from a cardiac arrhythmia) compromises the accuracy of hemodynamic measurements. Real-time MRI, coupled with ECG telemetry and semi-automated LV endocardial segmentation, can be used to identify multiple beat morphologies and derive global hemodynamic measurements for each beat.

ECG-gated cardiac MRI alone may be unable to capture the hemodynamics associated with arrhythmic events. As a result, values such as EF are acquisition dependent (the desired RR-duration can determine the arrhythmia rejection). By combining real-time volume measurements with ECG recordings, beat morphologies can be categorized and a more comprehensive evaluation of ventricular function during arrhythmia can be provided.

Deriving multiple cardiac biomarkers in patients with arrhythmias may improve risk assessment and clinical decision making. A prototype has been implemented in software on a computer from imaging data collected using magnetic resonance imaging.

These and other characteristic features will be apparent from the following detailed description.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 5A-C illustrates a 2D RR-duration plot.

DETAILED DESCRIPTION OF ILLUSTRATIVE EMBODIMENTS

Certain specific details are set forth in the following description with respect to FIGS. 1-2 to provide a thorough understanding of various embodiments. Certain well-known details are not set forth in the following disclosure, however, to avoid unnecessarily obscuring the various embodiments. Those of ordinary skill in the relevant art will understand that they can practice other embodiments without one or more of the details described below. Also, while various methods are described with reference to steps and sequences in the following disclosure, the description is intended to provide a clear implementation of embodiments, and the steps and sequences of steps should not be taken as being required.

Figure 1:
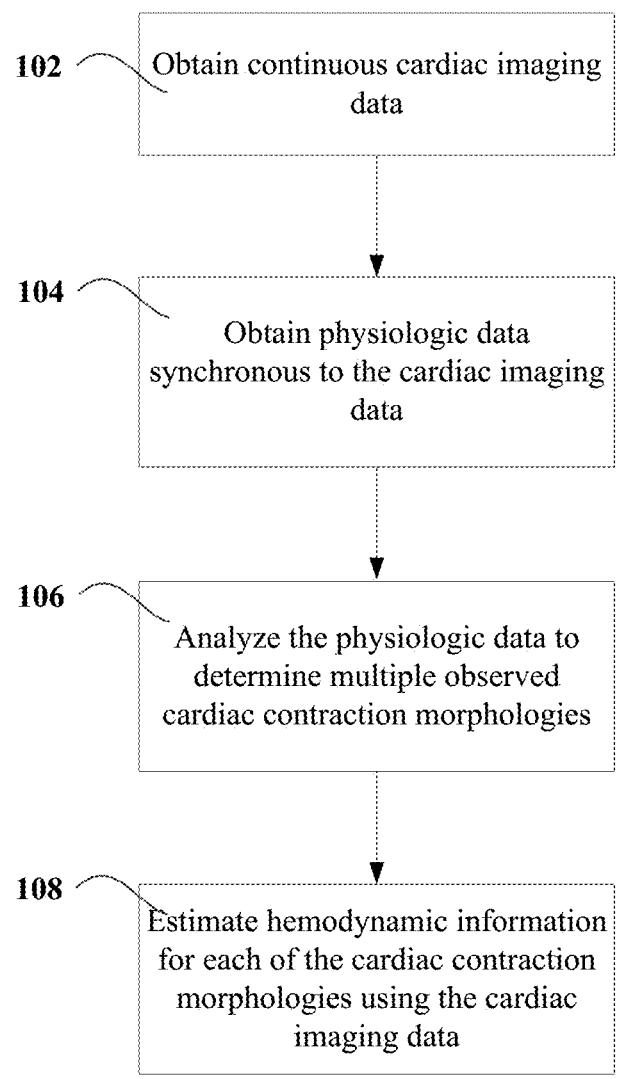
FIG. 1 illustrates a flow chart of an exemplary embodiment of the invention.
Figure 2:
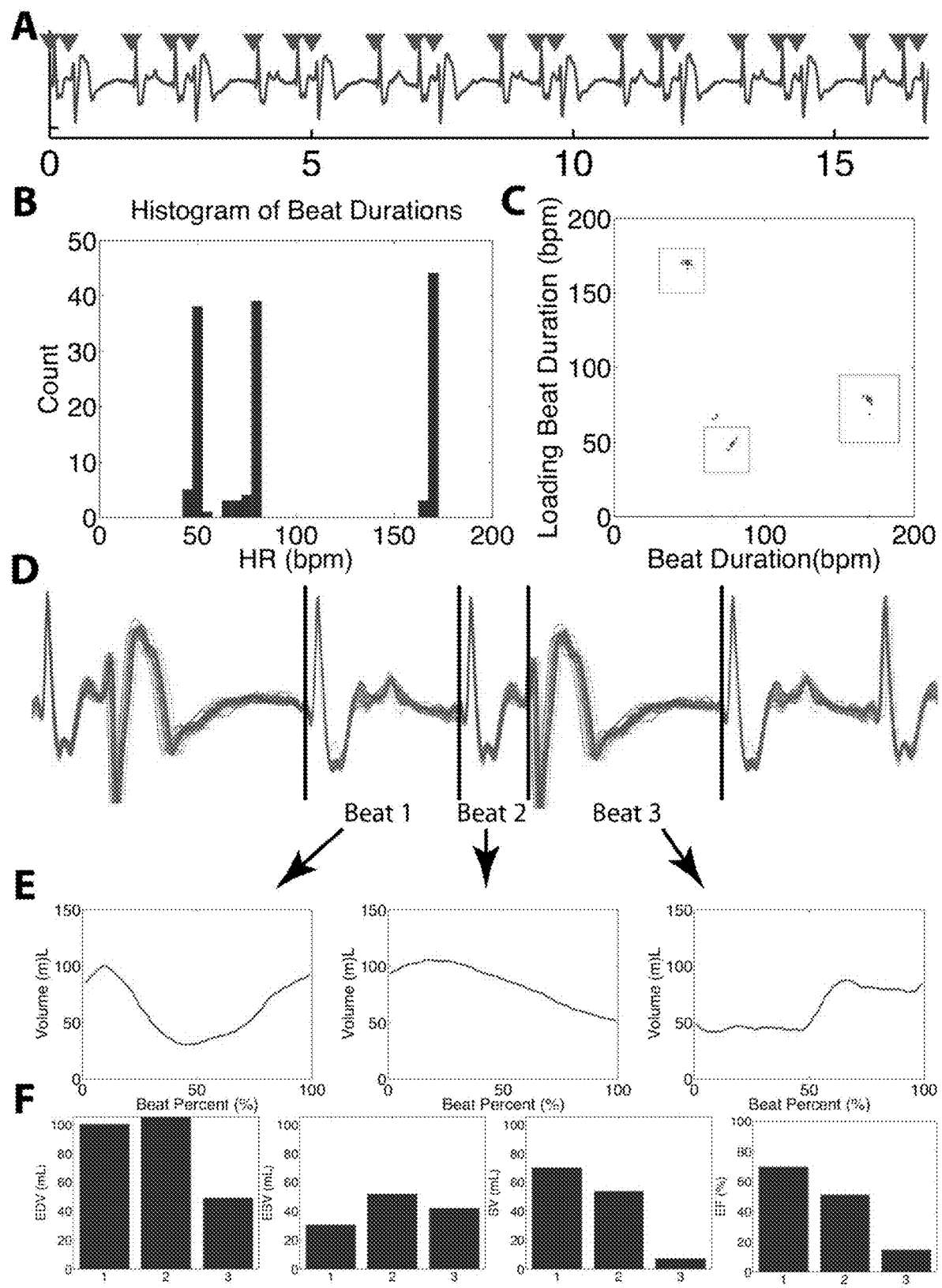
FIGS. 2A-F illustrate data obtained from patients with frequent premature ventricular contractions (PVCs).

FIG. 1 illustrates a flow chart of an embodiment of the invention.

In step 102, continuous cardiac imaging data is obtained. The continuous cardiac imaging data can be Left Ventricle (LV) or other heart chamber imaging data. In one embodiment, the continuous cardiac imaging data is MRI data. The continuous cardiac imaging data can be a Two-Dimensional (2D) multi-slice MRI acquisition, or a 2D golden angle radial acquisition. 2D slice imaging data allows for regional evaluation of contraction and conduction patterns. The imaging data can also be cardiac imaging data from Echocardiography, a computerized tomography (CT) scan or some other method. The cardiac imagining can be non-invasive or even invasive (such as from Transesophageal echocardiography (TEE)).

In step 104, physiologic data synchronous to the cardiac imaging data is obtained. The physiologic data can be a heart signal, an electrocardiogram (ECG) or some other type of physiologic data. Synchronization can be done using time-stamps.

In step 106, the physiologic data is analyzed to determine multiple observed cardiac contraction (beat) morphologies. Heartbeats can be categorized into morphologies or categories using classifiers.

In one multidimensional classifier, the duration (RR interval obtained from the physiologic data) of two consecutive beats, the current beat (beat 1) and the previous beat (beat 2) are measured. In this example, a particular cardiac contraction morphology can be defined as one that could be clustered in a 2-dimensional space (dimension 1=duration of beat 1, dimension 2=duration of beat 2) using a minimum and maximum duration threshold in each dimension.

In step 108, hemodynamic information is estimated for each of the cardiac contraction morphologies using the cardiac imaging data. For example, cardiac imaging data from the different cardiac contraction morphologies can be analyzed to get a determination of the ejection fraction for each cardiac contraction morphology.

The estimating of the hemodynamic information can be an estimation of global hemodynamic information for each beat morphology by combining regional hemodynamic estimates. Regional hemodynamic estimates can be from different image slices. The cardiac imaging data can be used to obtain the regional hemodynamic information.

A comprehensive hemodynamic quantification report can be created based on observed beat morphologies and global hemodynamic information. For example, a comprehensive ejection fraction estimate can be created from a weighted combination of the ejection fraction estimates of the different cardiac contraction morphologies. An example is described below.

A magnetic resonance imaging (MRI) method was used to acquire images of the heart in the short-axis orientation. The MRI pulse sequence used was a golden angle radial balanced steady-state free precession (bSSFP) data was acquired at multiple positions in the left ventricle (e.g. 10-13 slices to cover the heart).

Real-time images were reconstructed from magnetic resonance imaging data using a non-Cartesian, iterative sensitivity encoding (SENSE) algorithm, with 34 projections per frame and a sliding window of 1 (Gadgetron, National Institutes of Health).

Segmentation was performed using user-initialized region growing segmentation to trace the endocardial contour in each image frame and obtain a slice volume estimate for each image frame using software (ITK-SNAP, Philadelphia, Pa.).

Synchronous ECG data was recorded during the acquisition. Two synchronization approaches were utilized.

In the first approach, the MRI scanner assigned an ECG value to each segment of the MRI acquisition (a subset of the total image), resulting in synchronized ECG measurement. In this method, there is no additional synchronization or interpolation needed.

In the second approach, the ECG signal was written to a log file by the MRI scan. For each scan, a unique log file was generated. The 2D multi-slice acquisition was obtained without any interruptions to generate a continuous period of data sampling. A message was sent via the scan to the log file to indicate when the continuous sampling period beings and ends. This allowed for the precise period of ECG values during which scanning occurred to be identified.

Since the number of ECG data points acquired was uniformly sampled at 400 Hz, the ECG signal was interpolated to the sampling rate of the MRI scanner (~357 Hz) and an ECG value was assigned to each MRI data point.

A delay between the ECG and data sampling will result in slightly offset volume and ECG data, however, it will not affect the analysis of beat morphologies.

The ECG value synchronized to the middle data segment of a reconstructed image frame was matched to measured parameters from that slice, such as slice volume. Timestamps can be used for data synchronization to combine ECG data and MR image data. An additional challenge is that the ECG and MRI data is obtained using different systems of hardware and software with asynchronous clocks. Therefore, the absolute time for synchronization can be communicated between these two systems.

MRI data is acquired in a finite time period and therefore the acquired data does not correspond to a single instant in the ECG waveform; several ECG data are acquired for each MR image. In one embodiment, the image is equally weighted from all of the ECG data points and the temporal median was chosen to select the corresponding ECG.

For each ECG, the QRS complex labeled using a peak detection algorithm to identify the beginning and end of each cardiac cycle. Beats were categorized into morphologies or categories using multidimensional classifiers. In the simplest classifier, the duration (RR interval) of two consecutive beats, the current beat (beat 1) and the previous beat (beat 2) were measured. This part is further elucidated in FIG. 2.

Manual thresholding of the duration of beats 1 and 2 was used to group heartbeats into N morphologies, where N was chosen by the user.

A particular beat morphology was defined as one that could be easily clustered in a 2-dimensional space (dimension 1=duration of beat 1, dimension 2=duration of beat 2) using a minimum and maximum duration threshold in each dimension.

For example, beat 1 would be defined as having a beat duration of 600-800 ms with a prior beat duration of 600-800 ms.

Each beat morphology was defined by 4 total parameters. More parameters based on a longer beat history or other signal sources could be added to this approach (resulting in an M-dimensional space) where M is the total number of parameters. However, our results have shown that a 2D space with the parameters outline is sufficient to separate out the beat morphologies. Our method currently records 2 ECG signals (V1 and AVF) however processing has only relied on V1.

An automated or semi-automated clustering approach such as k-means could be utilized to group beats and then allow for manual refinement or may require a user to identify the number of morphologies they would hope to see grouped.

Additional physiologic data for multidimensional clustering or the use of automated clustering of heart rhythm morphology can be used.

For each beat morphology, a global volume estimate was obtained by summation of the slice volume curves associated with that morphology. There is intrinsic variation in the normal sinus RR interval, so a robust method to combine ECG data from multiple, different heart beats is used. In addition, when there is heart rate variability, the systolic and diastolic time periods to not scale linearly with the change in heart rate and therefore a nonlinear approach is used. In one embodiment, the ECG waveform can be temporally scaled using independent scaling of the systolic and diastolic periods.

Prior to summation, slice volumes for each morphology are transformed from a time domain to a percentage (%) cardiac cycle domain via a non-linear scaling of the heart beat duration. This is based on the well known phenomena where diastole shortens much more than systole to allow for faster heart rates.

In the case of multiple observations of a particular morphology in the same slice, the median value was utilized. In one embodiment, if a beat morphology occurs frequently, it will likely be observed multiple times in a single MRI slice. As a result, a particular beat morphology will be observed at all slices and often, multiple times in each slice. Therefore, a method to resolve the multiple observations can be used. In one embodiment, the inventors determine the median beat and use its observed slice volume. This reduces the potential corruption from a single outlying beat or error in segmentation.

In the case where a particular morphology was not observed in all slices, the morphology can be removed from further processing or the manual cut-offs can be modified to allow for a completed dataset. It is also possible to estimate a missing slice using information from neighboring slices or other prior information.

If a beat morphology is rare it is possible that it will not be observed at least one at each slice location. 'Forcing' a dissimilar beat morphology to fit into a morphology will result in corrupted volume estimation. Therefore, in this method, the inventors take a conservative approach and only describe the morphologies that are frequent enough to allow for observation of the beat morphology at each slice location as these are expected to have the largest clinical importance.

Hemodynamic measurements for each beat morphology such as end-diastolic volume (EDV), end-systolic volume (ESV), stroke volume (SV), and ejection fraction (EF) can be made based on the global volume curve.

Additional measures based on the prevalence of particular beat morphologies can also be incorporated. For example a temporal weighted average can be used to determine how 3 different morphologies can lead to an average EDV or EF.

Furthermore, the percentage of beats not assigned to a final morphology can be used to evaluate the effectiveness of the approach. If one morphology is observed across all slices but only accounts for a small percentage of the total beats, the hemodynamic values may not capture the patient's hemodynamics.

Slice by slice imaging allow for additional values to be generated. Specifically, the activation pattern can be visualized by comparing the change in volume in a slice to the change in the global volume and identify early or late activating regions. Temporally weighted estimate of function, percentage of assigned/unassigned beats, and activation pattern quantification can be used.

FIGS. 2A-F shows results obtained from clinical patient with frequent premature ventricular contractions (PVCs). FIG. 2A shows an ECG obtained with QRS (the name for the combination of three of the graphical deflections seen on a typical electrocardiogram) detection results at one slice location. FIG. 2B shows a histogram of RR-duration showing effect of PVCs. FIG. 2C shows a 2D plot of beat (x) and loading beat (y) durations allows for separation and identification of multiple beat morphologies. FIG. 2D shows 3 beat morphologies were identified in this patient. The ECGs associated with the morphologies are shown. The first beat morphology is a normal depolarization which occurs after a prolonged diastolic period, the second beat morphology is a normal contraction which is interrupted during diastole by a PVC contraction, and the third morphology is a PVC. In this patient, this 3 beat pattern is consistently repeated. FIG. 2E shows global volume obtained by slice volume summation for each morphology. FIG. 2F shows volumetric measurements made for each beat show large variations depending on the morphology For the example of FIGS. 2A-F, short-axis golden angle radial Balanced Steady-State Free Precession (bSSFP) projections (8000 projections/slice) were reconstructed using Gadgetron (non-Cartesian, iterative SENSE) with 34 projections per frame, and slice volume was measured via segmentation of LV endocardial contour with ITK-SNAP (software application used to segment structures in three-dimensional medical images). The ECG was synchronously recorded with the acquisition, and each image frame was assigned a time point on the ECG (~22 seconds/slice). QRS detection was used to identify cardiac cycles, and similar beats (across slices) were grouped via RR-duration of the beat of interest as well as the previous (loading) beat. The use of the loading beat duration allowed for accurate grouping of premature ventricular contractions (PVCs). For each beat morphology, global volume was obtained by summation of slice volume curves allowing for hemodynamic evaluation via EDV, ESV, SV, and EF.

10 patients were imaged: 5 in sinus rhythm, 3 with PVCs with 19%, 24%, and 33% prevalence, 1 in regular bigeminy, and 1 in irregular bigeminy (bigeminy is the continuous alternation of long and short heart beats). All beats detected beats were assigned a morphology, excluding the first beat of each acquisition since the loading conditions of these beats were unknown. A single beat morphology was observed in patients in sinus rhythm while patients with rhythm disturbances demonstrated multiple beat morphologies with large variations in measured volumes and EF.

FIGS. 2A-F show real-time and composite hemodynamic measurements in a patient with frequent PVCs (33%). In this patient, the SV and EF varied from 7.2-69.9 mL and 14.7-69.7% respectively, depending on the beat morphology. This variation suggests that cardiac cine (short movies that are able to show heart motion throughout the cardiac cycle), even with perfect arrhythmia rejection, misses important aspects of ventricular function in the presence of arrhythmias.

Figure 3:
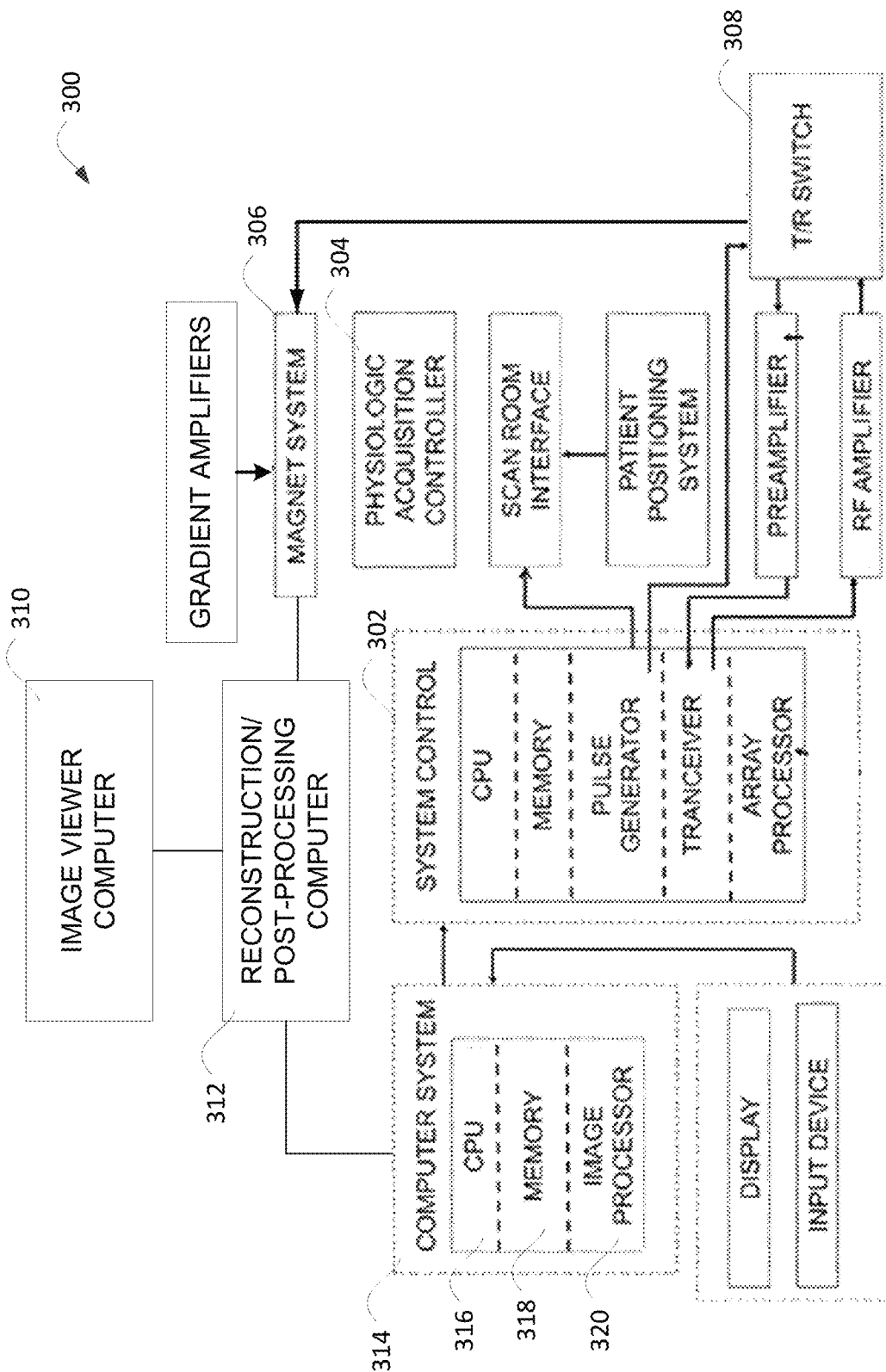
FIG. 3 is a diagram of an exemplary MRI device

FIG. 3 is a diagram of an exemplary MRI device 300 that can be used with the system and method described above. System control 302 is a controller for the MRI device. A physiologic acquisition controller 304 can include or be associated with a sensor to obtain physiologic data, such as heart data like an ECG.

An MRI scanner can scan a body part, such as the heart, to produce new MRI data. The MRI scanner can include magnet system 306 and Transmit/Receive (T/R) switch 308. A computer 310, 312, or 314 can analyze physiologic data to determine multiple observed cardiac contraction morphologies and estimate hemodynamic information for each of the cardiac contraction morphologies using the cardiac imaging data. The computer, such as computer 314, can include a processor 316 and memory 318. The computer can also include an image processor 320.

Additional Information

Premature ventricular complexes (PVC) are prevalent in the general population and are frequently associated with reduced ventricular function. Current echocardiographic and cardiovascular magnetic resonance imaging (CMR) techniques do not adequately address the effect of PVCs on left ventricular function.

Fifteen subjects with a history of PVCs undergoing CMR had real-time slice volume quantification performed using a real-time CMR imaging technique. Synchronization of real-time imaging with patient ECG allowed for different beats to be categorized by the loading beat RR-duration and beat RR-duration. For each beat type, global volumes were quantified and temporal averages were obtained using the frequency of each beat type. Different patterns of ectopy including isolated PVCs, bigeminy, trigeminy, and interpolated PVCs were observed. Global functional measurement of the different beat types based on timing demonstrated differences in stroke volume and cardiac output associated with different beats. A temporal average of function was quantified for each subject depending on the frequency of each observed beat type.

Application of real-time CMR imaging to patients with PVCs revealed differential contribution of PVCs to hemodynamics depending on timing and frequency.

Premature ventricular complexes (PVCs) are early electrical depolarizations originating in the ventricular myocardium, which can disrupt the coordinated electrical depolarization and mechanical contraction of the heart. Idiopathic PVCs may create variable symptoms and may cause a cardiomyopathy. Clinically, PVC-induced cardiomyopathy remains a diagnosis of exclusion and conventional imaging is often employed to rule out underlying disease Accurate assessments of left ventricular (LV) function using conventional segmented cardiovascular magnetic resonance (CMR) acquisitions are hindered by the presence of frequent PVCs due to the irregularly irregular rhythm. In conventional multi-shot 2D CMR, data for a single slice is acquired over multiple cardiac cycles and arrhythmias can lead to incorrect combination of data and cause considerable image corruption. Retrospective ECG-gated acquisitions can employ arrhythmia rejection to eliminate corruption due to ectopic beats. However, this approach discards data from ectopic contractions, can markedly prolong scan time during frequent PVCs and can result in respiratory motion artifacts due to unachievable breath-hold duration. Prospective ECG-gated acquisitions can also be utilized in patients with arrhythmias. If an arrhythmia is very regular, the acquisition window can be prolonged to acquire several beats after each QRS. Unfortunately, this approach is easily corrupted by any irregularity in the rhythm pattern and also markedly prolongs the scan time, making it sensitive to respiratory motion artifacts.

Single-shot (real-time) 2D CMR eliminates the need for combination of data acquired from multiple heartbeats and allows for observation of each cardiac contraction in a slice. The decreased spatial and temporal resolution associated with conventional real-time imaging results in a loss of slice volume accuracy. However, by combining non-Cartesian data acquisition, iterative image reconstruction, and semi-automated image processing, high spatial and temporal resolution real-time CMR image can be obtained and accurate measurement of 2D slice volume can be derived in a per-beat fashion.

In this work, we combine a previously-validated 2D real-time imaging technique with synchronous ECG recording, which allows for identification of different beat types based on RR intervals and the measurement of global volume via combination of 2D slice data for each beat type.

The prospective study was approved by the Institutional Review Board at the University of Pennsylvania and all subjects (n=15, 47.7±23.6 years old and 46.7% male) gave written informed consent. PVC burden was quantified via synchronously recorded ECG during CMR acquisition. Two subjects had no PVCs during the CMR exam despite a history of frequent PVCs. 13 patients had PVCs during real-time CMR (burden 25±14%, range 4-50%) and they demonstrated a range of arrhythmic patterns including bigeminy, trigeminy, and interpolated PVCs. Two of the 13 subjects (Subject 5 and 6) were imaged twice. Subject 5 was imaged pre and post PVC ablation and Subject 6 had two different PVC burdens and ectopic patterns during two imaging sessions.

CMR was performed on a 1.5 T imaging system (Avanto, Siemens Healthcare, Erlangen, Germany) equipped with nominal 40 mT/m magnetic field gradients, body RF transmit and a 32-channel, anterior and posterior RF receiver array.

Real-time data was obtained using a 2D, multi-slice, free-breathing balanced steady-state free precession (bSSFP) sequence with a golden-angle radial trajectory with the following imaging parameters, TE=1.4 ms, TR=2.8 ms, number of radial k-space data=128, FOV=220 mm-300 mm, pixel size=1.72–2.34×1.72–2.34 mm, bandwidth=1000-1221 Hz/pixel, slice thickness=8 mm, slice spacing=10 mm, and k-space sampling according to the golden-angle $\Phi$=111.25°. Imaging was performed in the short axis of the left ventricle. 6000-8000 radial projections (16-22 seconds) per slice were acquired.

The real-time image reconstruction and slice volume quantification methods have recently been validated in animal as well as in clinical patients. Briefly, image reconstruction was performed using a non-Cartesian SENSE algorithm in open-source software with 34 radial projections per image (image exposure time=95.2 ms) and maximal view sharing (frame rate=357 fps. Quantification of real-time images was performed through user-initialized active contour segmentation which has been shown to provide slice volume values comparable to manual segmentation using clinical tool. Papillary muscles were excluded from the segmentation using the feature image and manual correction. The basal slice was determined by identification of the slice with mitral valve annular plane at end-systole. LV slice volume was quantified from segmented data using the pixel size and slice thickness.

Electrocardiograms (ECGs) recorded in a magnetic field are distorted by the magnetohemodynamic effect, which limits the interpretability of the 3-lead ECG as compared with a 12-lead ECG. However, due to the need for ECG gating in cine CMR, robust 3-lead (ECG) acquisition, filtering, and real-time display are standard features of clinical CMR scanners. For this work, we implemented a logging algorithm to capture the ECG signal acquired during CMR. This results in synchronization between the ECG signal, real-time CMR image frames, and derived slice volume quantification as shown in FIG. 4.

Figure 4:
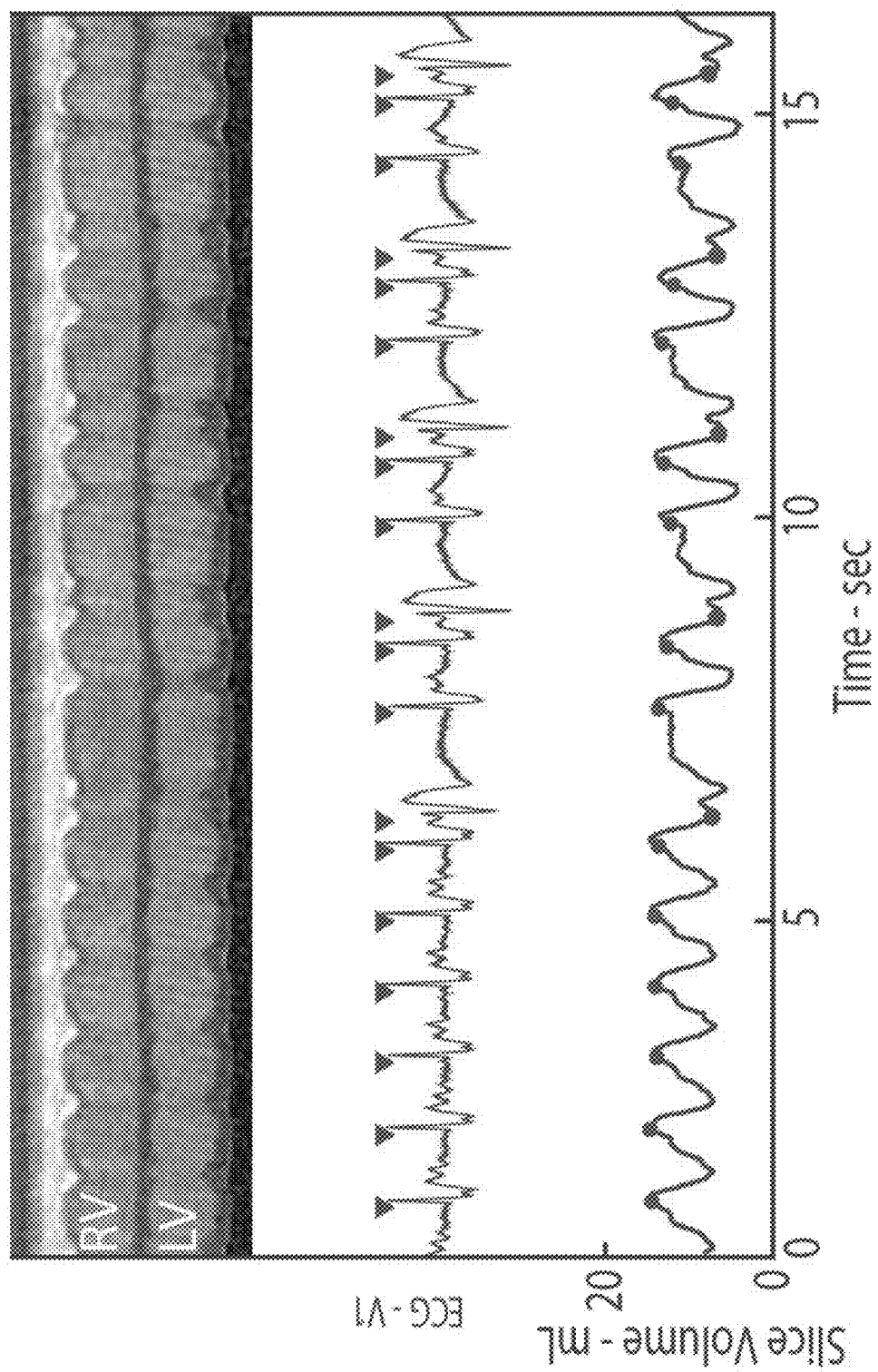
FIG. 4 illustrates a 2D real-time CMR imaging with synchronized ECG recording and measurement of slice volume over time.

FIG. 4 illustrates a 2D real-time CMR imaging with synchronized ECG recording and measurement of slice volume over time. Top row shows a projection through the heart where the contraction of the left ventricle begins in sinus rhythm and transitions to PVCs. The synchronously recorded ECG is shown in the middle row with the identification of the R-wave demarcated by a red triangle for sinus beats and green triangle for PVC beats. Quantification of slice volume (bottom row) allows for observation of the change in slice function due to arrhythmia. The slice volume associated with the R-wave (beginning of contraction) is shown via dots. For sinus contractions, the red dots occur close to the maximum slice volume (LV EDV). However, during a PVC, the green dots indicate PVC preload which may be substantially lower than the LV EDV.

The ECG distortion did not hinder detection of QRS peaks and allowed for quantification of RR durations. Although QRS morphology is distorted by the magnetic field, the distortion is consistent across the same PVC morphology, which allowed for identification of each PVC morphology in all patients as well as exclusion of premature atrial contractions (PACs). ECG recording was continuous and synchronous during the imaging of the entire short axis of the LV. PVC burden was quantified as the percentage of total beats.

Categorization of Beats After detection of the R-wave of the QRS complex via Pan-Tompkins algorithm implemented in Matlab (Mathworks, Natick Mass.), different beats were identified and categorized based on two measured RR-durations. As shown in FIG. 5, plotting the RR-duration of the prior (loading) beat versus RR-duration of the current beat allowed for clustering of different beats. Specifically, in sinus rhythm, a single cluster is observed (FIG. 5A). In patients with occasional PVCs, the clustering acts as robust arrhythmia rejection as only the sinus rhythm beats are sampled across all slices (FIG. 5B). Multiple clusters indicate the presence of distinctly different beat types and when a cluster is observed across all slice locations, global volume quantification of that beat type can be performed (FIG. 5C).

FIG. 5 illustrates a 2D RR-duration plot. Grouping of beat types based on current beat duration and loading (previous beat) duration. In FIG. 5A, a patient with sinus rhythm is shown with a single ECG and one 2D cluster. In FIG. 5B, a patient with a single PVC (green triangle) demonstrates how the algorithm can be used to provide arrhythmia rejection. When PVCs are infrequent, they were not observed at all slice locations and therefore did not result in global volume measurements. In FIG. 5C, a patient in trigeminy exhibits four beat clusters. Three clusters (with colored boxes) were observed at all slice locations. The remaining cluster (sinus-sinus) was only observed at a single slice location and is therefore excluded from further analysis.

For each ectopic contraction, there is a potential for four distinct beat types to be observed via the 2D clustering of loading RR-duration and the RR-duration of the current beat. The four beat types can be described as following. First, during normal sinus rhythm, there are two RR-intervals that are normal and the same: normal RR of the loading (preceding beat) and normal RR of the current beat (sinus-sinus beat). Second, when a PVC occurs, the sinus beat preceding the PVC is characterized by a normal loading RR followed by a short RR due to the premature depolarization (interrupted sinus beat). Third, the PVC beat is characterized by a short loading RR-duration followed by a long RR-duration for current beat (PVC beat). Finally, the sinus beat following a PVC is characterized by a long loading RR-duration followed by a normal RR-duration for the current beat (Post PVC-Sinus). In any particular patient, not all four beat types may be present or distinguishable using this 2D clustering with loading RR-duration and beat RR-duration. For example, in regular trigeminy, the pair of regular RR intervals (sinus-sinus) pattern does not occur. Similarly in bigeminy, only a PVC beat and a post-PVC sinus are observed, resulting in only two patterns: short-long RR and long-short RR. Even in irregular ectopic patterns where all four beat types occur, identification of these beat types based solely on two RR-durations may result in some beat types being classified together due to negligible differences in pre-load durations and beat durations.

Global Volume Estimation For each beat type, global volume over time was obtained via summation slice volumes over time across slice positions (FIG. 6). To account for small variations in RR-duration, non-linear beat duration normalization was performed prior to summation. Global volume over time was obtained only in beat types that were observed at all LV slice locations. If a particular beat type was observed multiple times in a single slice, the median value was used for global volume estimation.

Figure 6C:
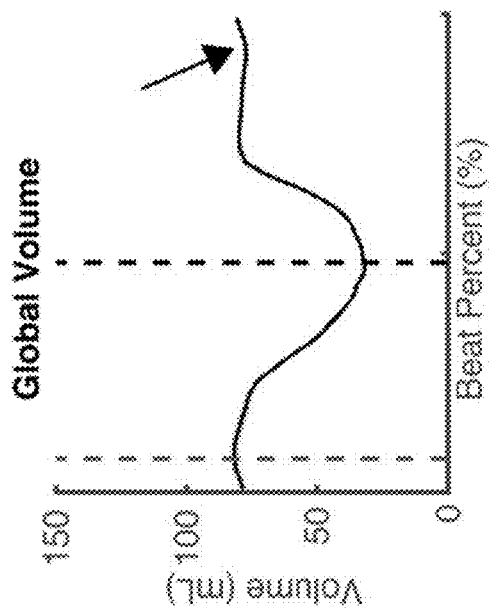
FIG. 6A-C shows global quantification of individual beat types.
Figure 6B:
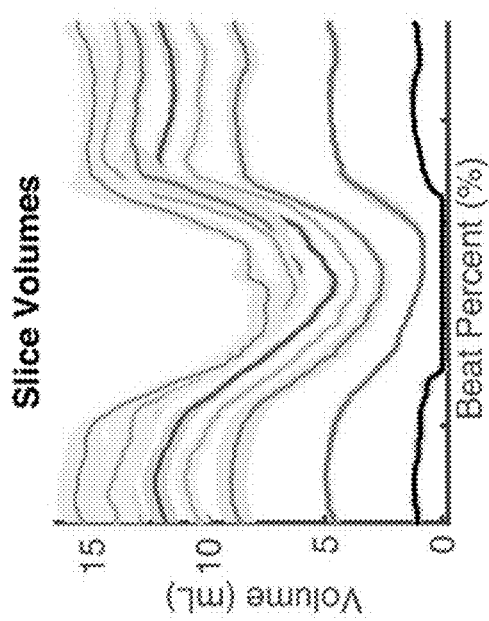
Figure 6A:
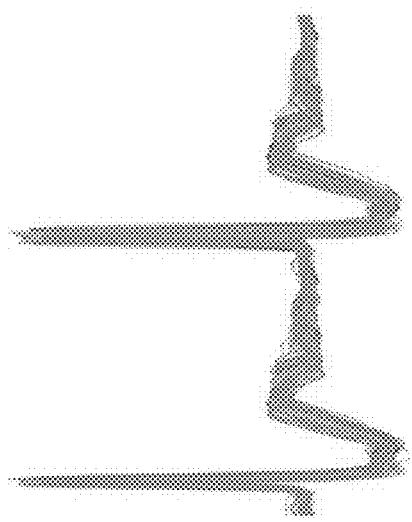

FIG. 6 shows global quantification of individual beat types. After definition of a cluster of beats with a similar loading beat duration and beat duration, the agreement in recorded ECG over all contractions was visualized (FIG. 6A). Summation of 2D slice volume results in global volume (FIG. 6B). Different color volume tracings represent different slices in the short axis of the LV. After summation, the EDV and ESV are determined on the global volume curve (FIG. 6C). The black arrow indicates a small increase in global volume due to atrial contraction.

Figure 7:
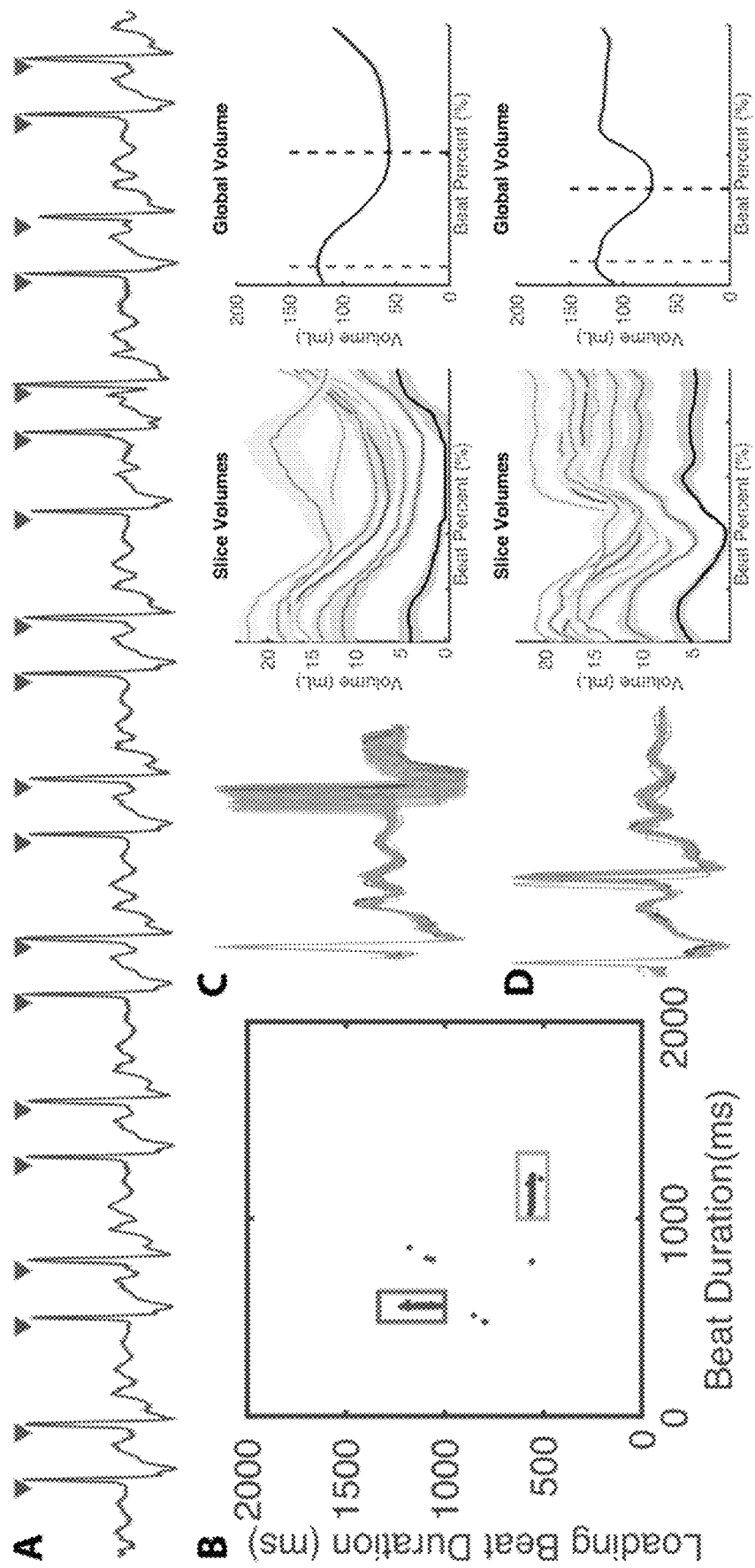
FIG. 7A-D illustrates LV function of a subject with bigeminy.

Global volume estimates made during PVCs are illustrated in FIG. 7. Subject 6 has a regular bigeminy pattern (FIG. 7A) and two beat types (clusters) are identified in FIG. 7B. FIGS. 7C and 7D illustrate the close agreement in ECG morphology across the observed beats. The global volume over time for each beat type is obtained by summation of slice volumes over time.

Quantification of Beat-by-Beat Function Global maximum volume (end diastolic volume (EDV) in sinus beats, loading volume in PVC beats), global minimum volume (end systolic volume (ESV) in sinus beats, smallest volume in the PVC beats), SV (maximum volume–minimum volume for the beat), and EF (SV/maximum volume) were obtained for each observed beat type. The prevalence of each type was used to obtain a temporally averaged estimate of function. The prevalence of each type was calculated as the percentage of beats identified in that beat type relative to the number of beats used for global volume estimation of all beat types. Using this approach, subjects where only a single beat type was imaged (arrhythmia rejection in Subjects 3 and 4) would have a temporal average EF equal to the EF measured in sinus beats. In 5 patients, LVEF obtained from clinically performed echocardiography exams were compared to MRI-derived values.

Evaluation of PVC Function Across Subjects To further understand the relationship of PVC timing to stroke volume produced by the PVCs, we plotted the SV of PVC contractions (normalized to the SV observed in sinus or interrupted sins beats in that subject) versus timing of PVC (normalized by the duration of sinus beats in the same subject). In the setting of bigeminy, the post-PVC contraction is used for normalization.

Intra- and Inter-Observer Variability The variation in the proposed approach stems mainly from the reproducibility of semi-automated segmentation of the individual LV slices. To quantify this variability, a mid-ventricular slice was re-segmented by the same observer as well as by a second observer for each imaging study (n=17), The slice EDV and ESV were estimated from 5 consecutive heartbeats as the mean maximum and mean minimum slice volume, respectively.

Statistical Analysis Two-tailed Student's t-test ($p<0.05$) was used to detect significant differences in the comparison of PVC burden between patients with normal and abnormal LV EF as well as differences between echo- and MRI-derived EF. One-way ANOVA amongst beat types (sinus, interrupted sinus, post-PVC sinus, and PVC) was performed to evaluate differences in SV and EF. Intra- and inter-observer reliability was quantified by coefficient of variation and Pearson correlation coefficient.

Results: In 5 subjects (Table 1, Patients 1-4 and 5 Post Ablation), only one beat type (sinus rhythm) was observed across all slice locations and thus one mode of ventricular volume and function was quantified (FIG. 6). These subjects were in sinus rhythm despite having a history of frequent PVCs (Patients 1 and 2) or had infrequent PVCs (4%, 7% and 8% PVC burden (Patient 3, 4, and 5 post ablation), which were not observed at all slice positions.

The remaining 10 subjects had frequent PVCs during imaging (13-50%). The PVC burden calculated based on the ECG differs from that prevalence of beat-types due to changes in rhythms (for example, sinus to trigeminy or bigeminy to trigeminy). As a result, the beat types described Table 1 may not contain all of the cardiac contractions; hence the sum of beat frequencies is less than 100%.

Subject 6 was imaged twice and was in regular bigeminy during the first real-time CMR. As a result, two beat types were observed (FIG. 7). The lower EF of the PVC was a result of less effective contraction with similar loading volume as the post-PVC sinus contraction, leading to a higher ESV. During the second imaging session, the same subject had frequent PVCs (40%) without a regular pattern. The PVCs were less effective toward cardiac output than the PVCs in bigeminy and contributed half of the SV compared to sinus beats (23.5 ml vs. 52.9 ml). Despite the difference in ectopic patterns at different time points, the temporally averaged EFs were similar (48.7% vs. 50.1%) in the two imaging sessions.

FIG. 7 illustrates LV function of a subject with bigeminy. A representative ECG (FIG. 7A) from a single slice demonstrates the bigeminy pattern. Two beat clusters are observed in the 2D plot of beat duration (FIG. 7B). As a result, two different global patterns can be quantified in FIG. 7C and FIG. 7D. Corresponding global volume measurements are found in Table 1 (Patient 6).

Figure 8:
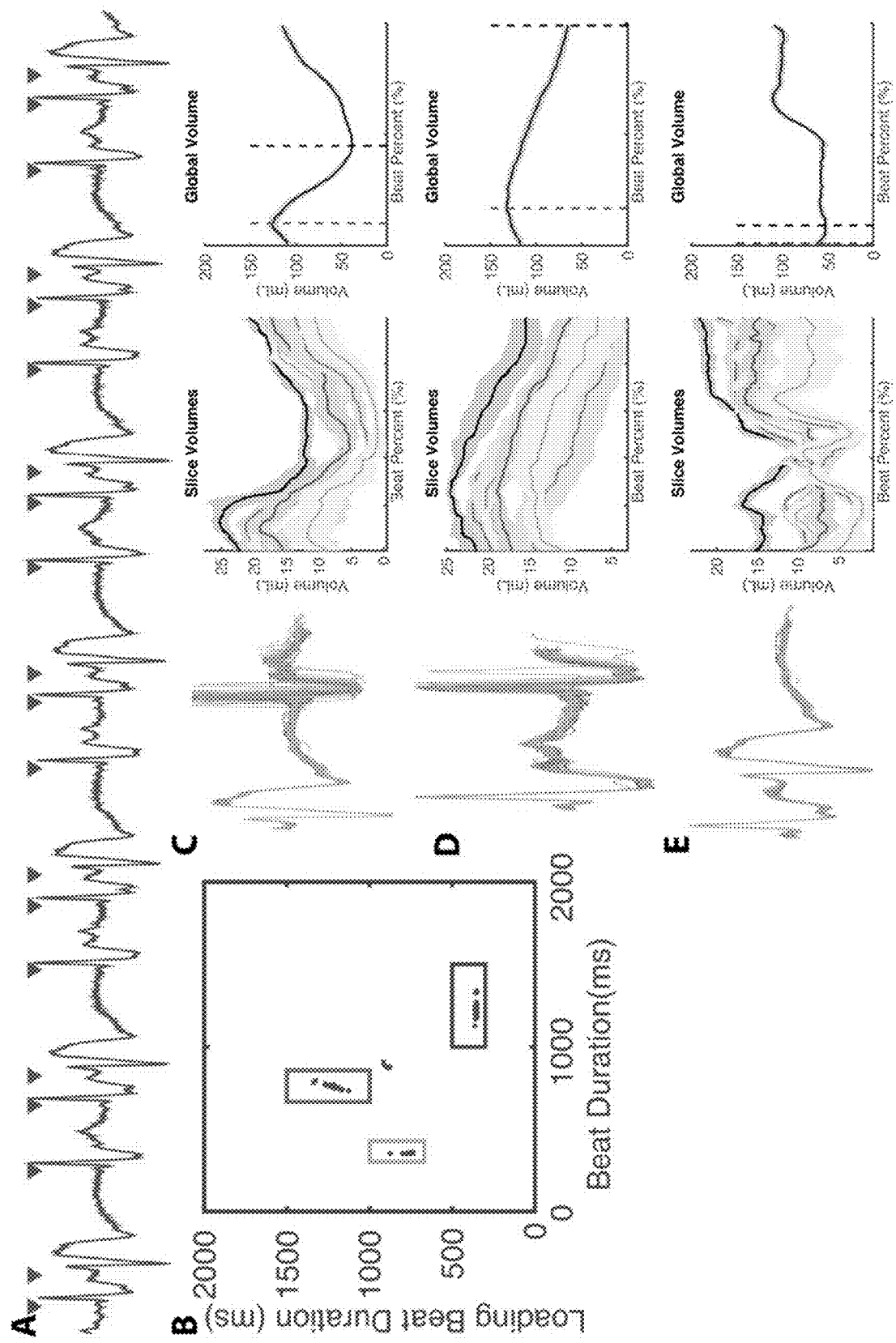
FIG. 8A-E illustrates LV function of a subject with trigeminy.

Subject 7 was in regular trigeminy during the real-time CMR, which resulted in 3 beat clusters (FIG. 8). In addition to the PVC, the 2D RR-duration plot allowed for the interrupted sinus cluster to be quantified separately from the post-PVC sinus and sinus-sinus cluster, shown in FIGS. 8C and 8D. ESV associated with the post-PVC sinus was lower than the interrupted sinus (38.7 ml vs. 65.8 ml) which resulted in a higher calculated EF (69.5 vs. 50.5%). The PVCs (FIG. 8E) in this pattern had a small stroke volume (9.6 ml). As a result, this patient demonstrated two contractions (interrupted sinus and post-PVC sinus) that produced high stroke volumes and one contraction (PVC) that produced very low stroke volume.

FIG. 8 illustrates LV function of a subject with trigeminy. Three types of beats (post-PVC sinus, interrupted sinus, and PVC) can be observed in the ECG (FIG. 8A). This leads to three distinct clusters and varying global volume measurements (FIGS. 8B-E). Global volume measurements are found in Table 1 (Patient 7).

Subject 8 had interpolated PVCs during the image acquisition (FIG. 9), which resulted in a unique pattern not described above. During interpolated PVCs, the PVC is an 'extra' depolarization in between sinus activity, which does not change the sinus P wave to P wave duration: in this case, there are two short RR intervals occurring sequentially. This type of PVC can be observed using the 2D RR-duration plot. The loading volume for the post-PVC sinus contraction (94.4 mL) decreased relative to normal sinus beats (126.8 mL). The post-PVC contraction resulted in a decrease in EF (34.6 vs. 42.6%). Furthermore, the PVC did not result in substantial SV (14.0 mL). As a result, interpolated PVCs resulted in a decreased SV in the PVC and post-PVC beats. The extra systole not only did not contribute much to cardiac output but also impaired the post-PVC sinus contraction by reducing preload for that beat.

Figure 9:
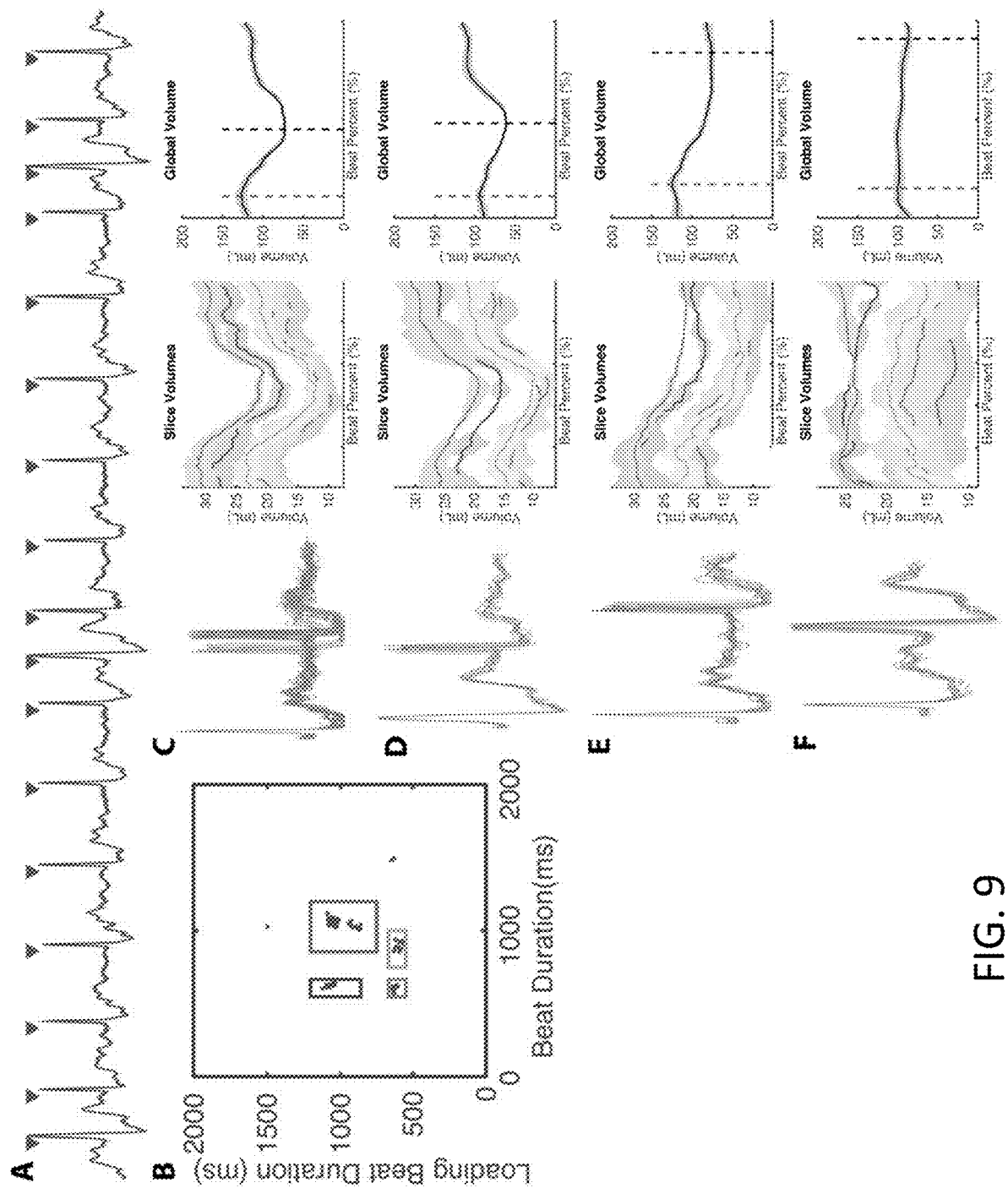
FIG. 9A-F illustrates LV function with interpolated PVCs.

FIG. 9 illustrates LV function with interpolated PVCs. The ECG (FIG. 9A) and 2D plot (FIG. 9B) depict 4 beat types: sinus rhythm (FIG. 9C), post-PVC sinus (FIG. 9D), interrupted sinus (FIG. 9E), and the interpolated PVC contractions (FIG. 9F). Global volume quantification suggests interpolated PVCs affect post-PVC loading and do not result in substantial stroke volume. Global volume measurements are found in Table 1 (Patient 8).

Subjects 9-15 and subject 5 prior to ablation had a variety of patterns including periods of bigeminy and trigeminy, as well as PVCs late in diastole. The different arrhythmia patterns resulted in different number of beat types being observed, which are also quantified in Table 1.

Amongst the 15 subjects, if we consider the LV function to be represented by the "normal depolarization" beats including sinus, interrupted sinus, and post-PVC sinus beats, then subjects 6, 7, 9, 10, 13, and 15 would have "normal" function. Their burden of PVCs measured by PVC frequency was not significantly different from the remaining subjects with "abnormal" LVEF (p=0.18). If we instead consider the average EF of all beats as the representation of LV function, only subjects 9 and 10 would have "normal" function. These two subjects had high burdens of PVCs (35% and 33%) but also had the 2 latest occurring PVCs (675 ms and 766 ms after the previous QRS, respectively) and therefore these PVCs produced stroke volumes that were similar to sinus beats, which limited the hemodynamic impact of the PVCs.

Figure 10:
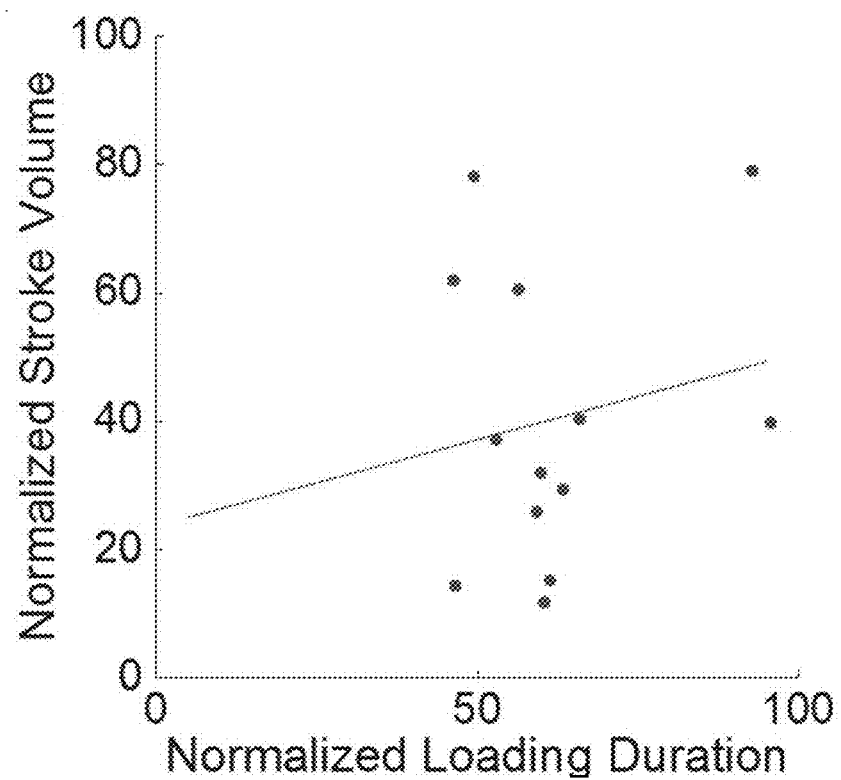
FIG. 10 illustrates normalized stroke volume vs. normalized loading duration.

To further understand the relationship of PVC timing to stroke volume produced by the PVCs, we plotted the SV of the PVC (normalized to the SV observed during sinus contractions that subject) versus timing of PVC (normalized by the duration of sinus beats in the same subject) as shown in FIG. 10. The SV of PVC was poorly correlated to the timing in the cardiac cycle (linear fit: slope=0.27, y-intercept=23.6, $R^2$=0.03, p-value=0.552).

There were statistically significant difference between SV (p<0.001) and EF (p<0.05) between PVC and all non-PVC beats. Differences between non-PVC beats (sinus, interrupted sinus, and post-PVC sinus) were not significant (SV p>0.88 and EF p-value>0.87).

5 patients had clinically performed cardiac echocardiograms preceding their MRI examination. The echo-derived EF was assessed using the biplane method and is shown in Table 1. When compared to non-PVC contractions, the values show close agreement ($R^2$=0.986, CoV=5.8%)

TABLE 2

Intra and Interobserver Variability in Measurement of Slice EDV and ESV.

| Cardiac Phase | Intraobserver | | Interobserver | |
|---|---|---|---|---|
| | CoV (%) | Pearson Coefficient | CoV (%) | Pearson Coefficient |
| ED | 6.5 | 0.982 | 6.4 | 0.982 |
| ES | 8.0 | 0.988 | 11.1 | 0.978 |

TABLE 1

Beat characteristics, volumetric measures, and weighted average of study subjects.

| Patient Number | Age | Sex | Arrhythmia Type | PVC Prevalence | Beat Type | Beat Duration (ms) | Beat Observations | EDV (mL) | SV (mL) | EF (%) | Frequency (%) | Temporal Average EF (%) | Echo-Derived EF (%) |
|---|---|---|---|---|---|---|---|---|---|---|---|---|---|
| 1 | 31 | F | History of PVC | 0% | Sinus | 849.6 | 207 | 81.1 | 44.0 | 54.3 | | | — |
| 2 | 22 | M | History of PVC | 0% | Sinus | 905.0 | 130 | 143.1 | 55.2 | 38.6 | | | 38 |
| 3 | 90 | F | PVC | 4% | Sinus | 740.1 | 20 | 152.3 | 59.2 | 38.9 | | | — |
| 4 | 56 | M | PVC | 7% | Sinus | 964.0 | 41 | 103.5 | 49.7 | 48.0 | | | — |
| 5 | 19 | F | Irregular Bigeminy | 41% | Post-PVC Sinus | 1010.5 | 66 | 162.2 | 59.3 | 36.5 | 11 | 23.0 ± 9.4 | 36 |
| | | | | | PVC | 666.3 | 66 | 145.6 | 24.0 | 16.5 | 22 | | |
| | | | Post Ablation | 8% | Sinus | 730.6 | 66 | 170.7 | 60.1 | 35.2 | | | |
| 6 | 28 | F | Bigeminy | 50% | Post-PVC Sinus | 1132.6 | 32 | 123.7 | 67.9 | 54.9 | 44 | 48.6 ± 6.3 | — |
| | | | | | PVC | 558.3 | 53 | 125.6 | 53.1 | 42.3 | 44 | | |
| | | | PVC | 40% | Post-PVC/Sinus | 1350.3 | 51 | 84.9 | 52.9 | 62.2 | 19 | 50.1 ± 15.3 | — |
| | | | | | Interrupted Sinus | 1012.0 | 41 | 102.3 | 63.2 | 61.8 | 32 | | |
| | | | | | PVC | 534.1 | 43 | 77.4 | 23.5 | 30.4 | 30 | | |
| 7 | 51 | M | Trigeminy | 33% | Post-PVC/Sinus | 1224.0 | 44 | 126.9 | 88.2 | 69.5 | 29 | 44.5 ± 22.5 | 65 |
| | | | | | Interrupted Sinus | 761.3 | 39 | 132.8 | 67.0 | 50.5 | 31 | | |
| | | | | | PVC | 353.9 | 11 | 62.5 | 9.6 | 15.3 | 31 | | |
| 8 | 58 | M | Interpolated PVC | 19% | Sinus | 1056.3 | 13 | 126.8 | 54.0 | 42.6 | 47 | 36.3 ± 10.1 | — |
| | | | | | Post-PVC Sinus | 594.1 | 12 | 94.4 | 32.7 | 34.6 | 13 | | |
| | | | | | Interrupted Sinus | 1056.3 | 54 | 124.3 | 49.2 | 39.6 | 16 | | |
| | | | | | Interpolated PVC | 625.5 | 18 | 100.0 | 14.0 | 14.0 | 14 | | |
| 9 | 59 | F | PVC | 35% | Post-PVC/Sinus | 1288.6 | 19 | 83.9 | 61.7 | 73.6 | 39 | 69.1 ± 8.8 | — |
| | | | | | Interrupted Sinus | 1131.4 | 48 | 85.5 | 63.1 | 73.9 | 13 | | |
| | | | | | PVC | 675.4 | 63 | 38.8 | 20.2 | 52.1 | 14 | | |
| 10 | 42 | F | Irregular Trigeminy | 33% | Post-PVC/Sinus | 967.8 | 38 | 65.8 | 42.6 | 64.8 | 22 | 61.7 ± 3.0 | 62 |
| | | | | | Interrupted Sinus | 825.2 | 102 | 72.5 | 45.1 | 62.3 | 29 | | |
| | | | | | PVC | 766.3 | 33 | 62.7 | 35.6 | 56.9 | 18 | | |
| 11 | 67 | M | PVC | 28% | Post-PVC/Sinus | 549.4 | 35 | 140.6 | 40.9 | 29.1 | 37 | 27.4 ± 5.2 | — |
| | | | | | Interrupted Sinus | 736.0 | 78 | 149.2 | 48.6 | 32.6 | 12 | | |
| | | | | | PVC | 703.5 | 56 | 110.7 | 19.4 | 17.5 | 13 | | |
| 12 | 19 | M | PVC | 25% | Sinus | 711.1 | 58 | 171.2 | 64.8 | 37.9 | 30 | 34.5 ± 11.0 | — |
| | | | | | Post-PVC Sinus | 1103.0 | 55 | 149.3 | 68.6 | 45.9 | 22 | | |
| | | | | | Interrupted Sinus | 739.8 | 36 | 166.8 | 62.8 | 37.7 | 23 | | |
| | | | | | PVC | 450.8 | 8 | 124.4 | 14.8 | 21 | | | |
| 13 | 56 | F | PVC | 24% | Sinus | 970.6 | 12 | 104.9 | 56.7 | 54.1 | 44 | 54.9 ± 5.9 | — |
| | | | | | Post-PVC Sinus | 1552.2 | 11 | 108.3 | 75.3 | 69.5 | 10 | | |
| | | | | | Interrupted Sinus | 970.6 | 111 | 122.4 | 66.6 | 54.4 | 15 | | |
| | | | | | PVC | 448.0 | 15 | 73.6 | 35.1 | 47.7 | 14 | | |
| 14 | 90 | M | PVC | 14% | Post-PVC/Sinus | 1106.2 | 14 | 126.6 | 65.1 | 51.4 | 69 | 47.4 ± 11.9 | 52 |
| | | | | | Interrupted Sinus | 936.9 | 98 | 127.1 | 65.5 | 51.5 | 9 | | |
| | | | | | PVC | 565.6 | 19 | 66.9 | 7.8 | 11.6 | 9 | | |
| 15 | 27 | F | PVC | 13% | Post-PVC/Sinus | 1292.5 | 18 | 87.2 | 49.0 | 56.2 | 64 | 50.8 ± 14.5 | — |
| | | | | | Interrupted Sinus | 977.7 | 207 | 99.2 | 57.5 | 58.0 | 12 | | |
| | | | | | PVC | 599.79 | 130 | 63.2 | 8.7 | 13.8 | 12 | | |

*EDV: End-diastolic volume,
†SV: stroke volume,
‡EF: ejection fraction,
§PVC: premature ventricular complexes The reproducibility results are shown in Table 2. Pearson coefficients values were high for both cardiac phases as well as intra- and inter-observer measurements.

Discussion: A variety of mechanisms have been proposed for PVC-induced cardiomyopathy including hemodynamic impairment, alterations in heart rate, vascular autonomic dysregulation, increased oxygen consumption, ventricular dyssynchrony, tachycardia-induced cardiomyopathy, or alterations in calcium and ionic currents, but it remains unclear which of these factors are the most relevant clinically. We present a novel method to assess PVC function, its contribution to cardiac output as well as the function of adjacent sinus depolarizations. Our findings suggest that different PVCs contribute different stroke volume and can potentially impact adjacent sinus depolarizations.

In assessing LV function in the presence of PVCs, there is currently no other published non-invasive method to assess the volumes and functions of PVCs in addition to sinus contractions. In echocardiography, which has been used in evaluating patients with suspected PVC-induced cardiomyopathy, PVCs are ignored in situations other than bigeminy (in which case sinus beats and PVC beats are averaged). Our method correlates closely with echocardiography in assessing the non-PVC beats.

The 2D real-time imaging method we utilized combines non-Cartesian k-space sampling and an iterative SENSE-based image reconstruction technique to improve the image quality (by reducing undersampling artifacts) and spatiotemporal resolution when compared to conventional real-time acquisitions. This allows for accurate estimation of slice and global volumes in sinus rhythm patients, when compared to standard cine acquisitions. However, other approaches including retrospective reconstruction of motion corrected data, compressed sensing reconstructions, and low-rank image reconstruction have been recently proposed to further improve spatiotemporal resolution and image quality. In the future, these techniques may allow for simultaneous imaging of multiple slices or true real-time 3D imaging.

In the patients with infrequent PVCs, our approach provided arrhythmia rejection similar to clinical CMR acquisitions where only the predominant contraction mode was quantified. However, our approach is more robust as conventional arrhythmia rejection can fail in several ways. First, conventional arrhythmia rejection utilizes the RR-duration to categorize beats in real-time and may have variable success depending on the ectopic morphology and frequency. Second, if the RR-duration acceptance window is too small, a high rejection rate will lead to prolonged breathholds and the potential for respiratory motion corruption. Third, not all PVCs may be reliably detected by the vector ECG since depolarizations can sometimes resemble a T-wave. Using the real-time imaging technique, our approach is not sensitive to any of these failure modes.

It has long been recognized that PVC burden is only one of the many factors contributing to impairment of LV systolic function in PVC-induced cardiomyopathy. PVC interpolation has been identified as an additional independent predictor but the hemodynamic mechanism has not been elucidated. In our study, we observed that a patient in regular bigeminy had two distinct beat types that both contributed substantial stroke volume. However, patients with other PVC patterns including trigeminy and interpolated PVCs demonstrated low stroke volume PVC beats. Furthermore, in the case of interpolated PVCs, the function of both the PVC as well the post-PVC contraction was impaired, which has not been previously reported.

This method can be used to evaluate patients before and after ablation therapy as illustrated in subject 5. With ablation therapy, there was reduction of PVC burden from 40% to 8%. The sinus contraction showed modest changes with increased SV from 59.3 mL to 60.1 mL but slightly decreased EF (36.5% to 35.2%) due to an increase in EDV (from 162.2 mL to 170.7 mL). The temporal average EF showed an increase from 23.0% to 35.2%. Long-term follow up is needed to elucidate which functional parameter best predict ablation outcome.

In addition to observing the PVC frequency and measuring the coupling interval of PVCs, this approach allows us to measure additional features of PVCs such as contractions which contribute significant stroke volume (>20 mL) (subjects 5, 6, 9, 10, and 13) and compare them to those that generate intermediate SV (subjects 8, 11, and 12) and low SV (<10 mL) (subjects 7, 14, and 15). This contribution to hemodynamics coupled with PVC frequency may be more important than frequency alone. For example, subject 6 had a PVC prevalence of 40-50%, but all the PVCs produced considerable stroke volume while subject 7 had a prevalence of 33% with PVCs that produced little stroke volume. It is believed that PVC-induced cardiomyopathy develops in a time-dependent fashion where the cumulative burden over time may play an important role. Future longitudinal work examining the impact of hemodynamics as well as frequency is needed.

Previously, it has been reported that PVCs with coupling intervals ≤600 ms have a lower mean LVEF but a recent study suggests a longer coupling interval leads to more dyssynchronous contraction. FIG. 10 explored the relationship between the timing of the PVC and the stroke volume produced in our patients. The correlation was poor and is likely due to additional factors which can impact SV such as origin of the PVC, the level of dyssynchrony associated with the PVC contraction, and the degree of underlying cardiomyopathy. Future studies are needed to examine these additional factors.

FIG. 10 illustrates normalized stroke volume vs. normalized loading duration. For patients with ectopic contractions the normalized stroke volume (percentage of stroke volume during sinus) was plotted as a function of normalized loading duration (percentage of loading duration for sinus contraction). Linear fit: slope=0.27, y-intercept=23.6, $R^2$=0.03, p-value=0.552.

To understand the hemodynamics of other arrhythmias such as atrial fibrillation, pacing models of otherwise healthy, instrumented animals has been previously developed. Our technique allows for evaluation of patients without the need for instrumentation as the ECG system and the imaging can be utilized to obtain both timing and hemodynamic information.

Some of the observations made in these prior studies were not observed in our patients. For example, we observed very small changes in EF after ectopic contractions while earlier work describes substantial post-extrasystolic potentiation. This discrepancy may be due to different measurement techniques or different patient populations.

Animal pacing models have also been utilized to better understand the myocardial dysfunction caused by PVCs. These models have found changes in global LV dimensions and function after 2-4 weeks of pacing with bigeminy that were programmed with a short coupling interval. These animal models suggest that PVCs can cause a reversible cardiomyopathy in structurally normal hearts but the question of what differentiates benign PVCs and myopathy-causing PVCs remains unanswered.

There are limitations to the study. First, the entire heart is acquired with a slice-by-slice 2D real-time imaging technique. In patients with infrequent PVCs, PVCs might not occur at all slice positions, which limits the quantification of rare PVCs. In these instances, quantitative values are similar to those obtained using conventional cine CMR with arrhythmia rejection. Future development of 3D real-time imaging or prolonged scans in these patients would allow for analysis of these infrequent PVCs.

A second limitation of this study is the potential impact of respiratory motion on measured cardiac function. We performed the real-time acquisition during free respiration to minimize the overall acquisition time. We did not use a respiratory window since it would reduce the number of observed beats and would compromise our ability to observe multiple beat types across slice locations. However, the potential effect of respiratory motion is likely small because large variations were not present in the slice volume curves (as shown in FIGS. 3-6). Furthermore, recent publications indicate that the effect of respiratory position on LV volume quantification is negligible, potentially due to a predominant in-plane as opposed to through-plane motion. However, changes in intrathoracic pressure will affect cardiac loading and therefore, imaging during breathholds or selection of images based on respiratory motion could be employed in future studies to minimize this effect.

We have presented a novel CMR-based method to assess LV function in subject with frequent ventricular ectopy, which provides volumetric assessment of multiple beat types. This method revealed that different PVC patterns contribute differently to hemodynamics depending on the timing and frequency of the PVCs. Our findings allowed for accurate interrogation of the LV function during PVCs in each individual patient and may provide new insight into PVC-induced cardiomyopathy and symptoms associated with PVCs.

LVEF is determined by LV stroke volume over LV preload (this is end-diastolic volume in sinus and pre-ejection volume in PVC beats). Post-extra systolic potentiation (PESP) has been described as a function of loading conditions (increase preload or decrease afterload), an artifact, or a real phenomena.

There remains a debate over whether or not contractility increases stems from the fact that an increase in SV may or may not be associated with an increase in EDV. The ability of ventriculography or instrumented measurements in animals to precisely measure volume is questionable. Using our method to measure volume, which does not make any assumptions, we have found that the LV preload is increased as well as stroke volume in post-PVC sinus beat and the EF turned out to be similar to that of the sinus beat. Our patient cohort includes patients with aortic stenosis, mitral regurgitation, and underlying cardiomyopathy with PVCs. The difference of our results as compared to previous literature might be due to different measurement technology and/or different patient populations. We will have to study more patients in different disease states to understand this further.

It will also be appreciated that the methods described herein may be implemented in software that operates on a processor that executes instructions stored in a memory component. The processor may include a standardized processor, a specialized processor, a microprocessor, or the like. The processor may execute instructions including, for example, instructions for implementing the method as described herein. On the other hand, the memory component stores the instructions that may be executed by the processor. The memory component may include a tangible computer readable storage medium in the form of volatile and/or nonvolatile memory such as random access memory (RAM), read only memory (ROM), cache, flash memory, a hard disk, or any other suitable storage component. In one embodiment, the memory component may be a separate component in communication with a processor, while in another embodiment, the memory component may be integrated into the processor. Such non-transitory memory components may be used as a computer readable storage device to store the instructions for implementing the methods and software features described herein.

Those skilled in the art also will readily appreciate that many additional modifications are possible in the exemplary embodiment without materially departing from the novel teachings and advantages of the invention. Accordingly, any such modifications are intended to be included within the scope of this invention as defined by the following exemplary claims.

What is claimed:

1. A method for evaluating hemodynamic function of a heart by:
   obtaining cardiac imaging data;
   obtaining physiologic data synchronous to the cardiac imaging data;
   analyzing the physiologic data to determine multiple cardiac contraction morphologies, wherein each of the cardiac contraction morphologies is indicative of a different beat pattern in the physiologic data determined based on one or more first parameters;
   estimating hemodynamic information for each of the cardiac contraction morphologies using the cardiac imaging data; and
   determining a second parameter based on a combination of the hemodynamic information estimated for each of the cardiac contraction morphologies.

2. The method of claim 1, wherein estimating the hemodynamic information includes estimating global hemodynamic information for each cardiac contraction morphology by combining regional hemodynamic information.

3. The method of claim 2, wherein the cardiac imaging data is used to obtain the regional hemodynamic information.

4. The method of claim 3, further comprising producing a comprehensive hemodynamic quantification report based on the cardiac contraction morphologies and the global hemodynamic information.

5. The method of claim 1, wherein the cardiac imaging data comprises heart chamber imaging data.

6. The method of claim 1, wherein the cardiac imaging data comprises a two-dimensional 2D multi-slice MRI acquisition.

7. The method of claim 1, wherein the cardiac imaging data comprises a 2D golden angle radial acquisition.

8. The method of claim 1, wherein the physiologic data comprises electrocardiogram (ECG) data.

9. The method of claim 1, wherein the cardiac imaging data comprises 2D slice imaging data that allows for regional evaluation of contraction and conduction patterns.

10. The method of claim 1, wherein the second parameter comprises an ejection fraction that is determined based on a weighted average of the hemodynamic information for each of the cardiac contraction morphologies.

11. The method of claim 1, wherein the cardiac contraction morphologies are determined using multidimensional classifiers.

12. A computer adapted to evaluate hemodynamic function of a heart, the computer including a memory and a processor, the processor adapted to:
   obtain cardiac imaging data;
   obtain physiologic data synchronous to the cardiac imaging data;
   analyze the physiologic data to determine multiple cardiac contraction morphologies, wherein each of the cardiac contraction morphologies is indicative of a different beat pattern in the physiologic data determined based on one or more first parameters;

estimate hemodynamic information for each of the cardiac contraction morphologies using the cardiac imaging data; and determine a second parameter based on a combination of the hemodynamic information estimated for each of the cardiac contraction morphologies.

13. The computer of claim 12, wherein estimating the hemodynamic information includes estimating global hemodynamic information for each cardiac contraction morphology by combining regional hemodynamic information.

14. The computer of claim 13, wherein the cardiac imaging data is used to obtain the regional hemodynamic information.

15. The computer of claim 13, wherein the processor is further adapted to produce a comprehensive hemodynamic quantification report based on the cardiac contraction morphologies and the global hemodynamic information.

16. The computer of claim 12, wherein the cardiac imaging data comprises heart chamber imaging data.

17. The computer of claim 16, wherein the heart chamber imaging data comprises magnetic resonance imaging (MRI) data.

18. The computer of claim 12, wherein the cardiac imaging data comprises a two-dimensional 2D multi-slice MRI acquisition.

19. The computer of claim 12, wherein the cardiac imaging data comprises a 2D golden angle radial acquisition.

20. A non-transitory computer-readable medium storing computer-executable instructions that, when executed by one or more processors, cause:

obtaining cardiac imaging data;

obtaining physiologic data synchronous to the cardiac imaging data;

analyzing the physiologic data to determine multiple cardiac contraction morphologies, wherein each of the cardiac contraction morphologies is indicative of a different beat pattern in the physiologic data determined based on one or more first parameters;

estimating hemodynamic information for each of the cardiac contraction morphologies using the cardiac imaging data; and determining a second parameter based on a combination of the hemodynamic information estimated for each of the cardiac contraction morphologies.

* * * * *